United States Patent
Scholz et al.

(10) Patent No.: US 6,641,825 B2
(45) Date of Patent: Nov. 4, 2003

(54) SKIN CLEANSING GEL HAVING A HEATING EFFECT

(75) Inventors: Wolfhard Scholz, Krefeld (DE); Katrin Meyer zu Schlochtern-Maric, Nürnberg (DE); Armin Wadle, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/231,979

(22) Filed: Aug. 30, 2002

(65) Prior Publication Data

US 2003/0108506 A1 Jun. 12, 2003

Related U.S. Application Data

(63) Continuation of application No. PCT/EP01/01882, filed on Feb. 20, 2001.

(30) Foreign Application Priority Data

Mar. 1, 2000 (DE) ......................................... 100 09 252

(51) Int. Cl.[7] .................................................. A61K 7/48
(52) U.S. Cl. ....................... 424/401; 424/685; 424/698; 424/709
(58) Field of Search ............................... 424/401, 685, 424/698, 709

(56) References Cited

U.S. PATENT DOCUMENTS

| 4,898,690 A | * | 2/1990 | Bitter et al. ................. 510/135 |
| 5,538,720 A | | 7/1996 | Jendryssek-Pfaff et al. |
| 5,747,004 A | | 5/1998 | Giani et al. |

FOREIGN PATENT DOCUMENTS

| BE | 791 366 | 5/1973 |
| DE | 23 17 140 | 10/1982 |
| DE | 31 41 746 | 5/1983 |
| DE | 196 24 870 | 1/1998 |
| EP | 0 518 721 | 12/1992 |
| EP | 0 950 400 | 10/1999 |
| WO | WO 93/08793 | 5/1993 |
| WO | WO 97/02802 | 1/1997 |
| WO | WO 97/30148 | 8/1997 |

OTHER PUBLICATIONS

JP 11349443 Abstract( Dec. 1999).*

* cited by examiner

*Primary Examiner*—Jyothsna Venkat
(74) *Attorney, Agent, or Firm*—Stephen D. Harper; Glenn E. J. Murphy; Gregory M. Mill

(57) ABSTRACT

A gentle skin cleansing gel is provided containing as an ingredient, water soluble salts having a negative enthalpy in solution, which when mixed with water release heat which improves the cleansing effect and the release of perfumes creating a pleasant effect on the skin.

13 Claims, No Drawings

SKIN CLEANSING GEL HAVING A HEATING EFFECT

CROSS REFERENCE TO RELATED APPLICATIONS

This application is a continuation under 35 U.S.C. §365 (c) and §120 of International Application No. PCT/EP01/01882 filed Feb. 20, 2001 and under §119 of German Patent Application No. 100 09 252.7 filed Mar. 1, 2000.

FIELD OF THE INVENTION

This invention relates to a gentle skin cleansing gel which, for use, is mixed with water and releases heat in the process. The heat released creates a sensorially pleasant impression on the skin, improves the cleansing effect, enhances the release of perfumes and leads to an improved effect of the skin-care ingredients present.

BACKGROUND OF THE INVENTION

The use of water-free salts with a negative enthalpy of solution which release heat of hydration when dissolved in water for the production of cosmetic preparations which heat up in use has been repeatedly described. DE 2317140 C2 describes water-based skin and hair treatment preparations which are heated just before use by addition of calcium chloride or magnesium sulfate. DE 19624870 A1 and WO 97102802 A2 describe dental care preparations which release heat on contact with water or saliva during brushing of the teeth. WO 93/08793 A1 describes a skin cleanser which may be used, for example, as a face mask and which contains a dehydrated molecular sieve in a water-free carrier as heat-releasing component.

However, these known preparations are unsuitable for use as skin cleansers, for example in the form of liquid or paste-form preparations of the liquid soap or washing paste type because they do not generate enough foam so that satisfactory cleansing of even relatively heavily soiled skin is not achieved.

Accordingly, there was a need to develop a skin cleanser in the form of a liquid or high-viscosity gel-form preparation which could be used like a normal liquid soap or a hand washing paste and which, in use, would generate a rich foam and at the same time so much heat that a sensorially pleasant feeling on the skin and deep-pore cleansing of the skin would be obtained.

SUMMARY OF THE INVENTION

The problem stated above has been solved by a cleansing gel which releases heat of hydration when mixed with water and which consists of a water-free liquid carrier and powder components dispersed therein, characterized in that it contains
(A) at least 40% by weight of water-miscible hydroxyl compounds selected from glycols, glycol ethers and polyols containing 2 to 6 carbon atoms, polyalkylene glycols with molecular weights of up to 1,000 D and mixtures thereof,
(B) at least 5% by weight of anionic, zwitterionic, ampho-teric or nonionic surfactants,
(C) at least 5% by weight of dispersed, particulate, water-soluble salts with a negative enthalpy of solution (in water) and
(D) at least 0.1% by weight of a water-soluble thickener dissolved in the carrier or at least 1% by weight of a particulate thickener dispersed in the carrier or both.

DETAILED DESCRIPTION OF THE INVENTION

In the context of the invention, a carrier liquid is regarded as water-free if it contains so little water that the hydrating salts dispersed therein do not undergo significant hydration.

Water-miscible hydroxyl compounds in the context of the invention are, above all, glycols, glycol ethers and polyols containing 2 to 6 carbon atoms. Accordingly, suitable glycols are ethylene glycol, propanediols and butanediols. Suitable glycolethers are, for example, ethyl glycol, ethyl diglycol, diethylene glycol, triethylene glycol and dipropylene glycol. Suitable polyols are, for example, glycerol, erythritol, pentaerythritol, trimethylol propane, diglycerol and sorbitol. Suitable polyalkylene glycols are, for example, the liquid polyethylene glycols, the polypropylene glycols and the addition products of ethylene oxide onto propylene glycol or onto polypropylene glycols with molecular weights of up to 1,000 D. Monohydric alcohols such as ethanol or isopropanol, for example, may also be present in limited quantities of up to about 5% by weight.

These water-miscible hydroxyl compounds are preferably present in a quantity of 50 to 70% by weight of the cleansing gel. The consistency and the dissolving and dispersing behavior of the carrier can be influenced through the type and quantity of the water-miscible hydroxyl compounds. In addition, some of these hydroxyl compounds also have a negative enthalpy of mixing with water, i.e. heat is released on mixing with water. For this reason, it is preferred to use mixtures of two or more different hydroxyl compounds to obtain an optimal application profile. Mixtures of 1,2-propylene glycol, 1,3-butylene glycol, polyethylene glycol and ethoxydiglycol are particularly suitable carriers.

Suitable anionic surfactants are any surfactants of which the surface activity is attributable to an anion distinguished by a preferably linear alkyl or acyl group containing 10 to 18 carbon atoms which is linked to a sulfate, sulfonate, phosphate or carboxylate group. Particularly suitable anionic surfactants are foaming types such as, for example, the alkyl sulfates, the alkanesulfonates, the α-olefin sulfonates, the acyl isethionates, the acyl taurides, the acyl sarcosides, the sulfosuccinic acid monoalkyl ester salts and the alkyl polyglycol ether carboxylates in the form of their alkali metal, magnesium, ammonium or alkanolammonium salts. Anionic surfactants obtainable in water-free fine-particle form are preferably used. These are generally the sodium salts of the anionic surfactants mentioned. Suitable zwitterionic surfactants are, above all, the betaine surfactants, for example $C_{12-18}$ alkyl dimethyl acetobetaine, cocoamidopropyl dimethyl acetobetaine, imidazolinium betaines and sulfobetaines containing a preferably linear $C_{10-18}$ alkyl or acyl group. Particularly suitable betaine surfactants are, above all, those obtainable in water-free, fine-particle form. A particularly suitable product is, for example, the cocoamidopropyl betaine marketed as Tego Betain CKD (N-N-dimethyl-N-lauroylamidopropyl)-ammoniumacetobetaine).

Ampholytic surfactants are understood to be surfactants which, besides a preferably linear $C_{8-18}$ alkyl or acyl group, contain a protonatable amino group and a carboxyl group and which are capable of forming inner salts. Suitable ampholytic surfactants are, for example, N-($C_{12-18}$)-alkyl-N-methyl glycine, N-($C_{12-18}$)-acylaminopropyl-N-methyl glycine, N-($C_{12-18}$)-acylaminoethyl-N-methyl glycine, N-($C_{12-18}$)-acylaminopropyl-N-hydroxyethyl glycine, 2-($C_{12-18}$)-alkyl carboxymethyl-3-hydroxyethyl imidazoline and 2-N-($C_{8-18}$)-alkylaminoethanecarboxylic acid.

Nonionic surfactants are surfactants which contain a lipophilic, preferably linear $C_{8-22}$ alkyl or acyl group and, as a hydrophilic group, a glucoside or polyglucoside group, a glycerol or polyglycerol group, a sorbitan group or a polyglycol ether group or several of these groups. Suitable nonionic surfactants are above all those which are available in water-free form, for example products of the addition of ethylene oxide onto fatty alcohols, fatty acids, fatty acid mono- or diglycerides, onto fatty acid alkanolamides, onto sorbitan fatty acid esters, onto methyl glucoside fatty acid esters or onto alkyl glucosides. Another particularly suitable group of nonionic surfactants are the silicone copolyols marketed, for example, under the name of Dow Corning Surfactant (Dow Corning) or Abil (Goldschmidt).

In one preferred embodiment, the cleansing gel according to the invention contains an anionic or zwitterionic surfactant or a mixture of such surfactants in a quantity of 10 to 30% by weight as surfactant.

Hydrating salts with negative enthalpy of solution are understood to be water-soluble salts which dissolve in water and release heat in the process. This is generally the case when hydrates are formed during dissolution and the heat of formation of these hydrates is greater than the heat consumed in overcoming the lattice energy. The hydrating salts are generally completely or partly dehydrated salts which form hydrates in water. Such salts are, for example, ortho- and pyrophosphates, carbonates and sesquicarbonate, borates, chlorides and sulfates of alkali metals, for example sodium. Other suitable salts are alkali metal citrates and acetates. Other suitable salts are zinc citrate, zinc sulfate, zinc nitrate, calcium chloride, calcium sulfate, magnesium chloride, magnesium sulfate and aluminium sulfate.

In a preferred embodiment of the invention, sodium, magnesium or aluminium sulfate or a mixture thereof in a quantity of 5 to 20% by weight is present as the hydrating salt. It is important in this regard to ensure that salts with a high heat of dissolution are not used in too large a quantity so as to prevent the unpleasant generation of heat on the skin in use. Accordingly, $MgSO_4$ (anhydrous), for example, should be used in quantities of not more than 15% by weight.

The gel-like consistency of the cleanser according to the invention can be controlled through the use of suitable thickeners. The viscosity of the product should preferably be higher than 2 Pa·s (as measured with a Brookfield RTV-Helipath rotational viscosimeter, spindle D, 20 r.p.m., 20° C.). For the application of the cleansing gel according to the invention from tubes or flexible plastic dispensing bottles, a viscosity of more than 5 Pa·s and more particularly in the range from 10 to 50 Pa·s is preferred.

The thickeners dissolved in the carrier are normally organic hydrocolloids, i.e. natural or synthetic polymers which swell or dissolve in water and which can be dissolved in the carrier liquid consisting essentially of the above-mentioned hydroxy compounds. Suitable dissolved thickeners are, for example, nonionic polysaccharide derivatives, such as, for example, hydroxypropyl cellulose, hydroxypropyl starch, hydroxypropyl guar, or synthetic polymers, such as polyvinyl pyrrolidone, polyvinyl alcohol or polyacrylamide. In a preferred embodiment, a nonionic polysaccharide derivative in a quantity of 0.1 to 1% by weight is present in the cleansing gel according to the invention as the thickener dissolved in the carrier.

Suitable particulate thickeners dispersed in the carrier are, for example, layer silicates, such as clays (kaolins, montmorillonites) for example, or amorphous silicas, such as pyrogenic silicas (Aerosil) for example, or particularly fine-particle silica gels. In a preferred embodiment, the cleansing gel according to the invention contains an amorphous silica in a quantity of 1 to 5% by weight as the thickener dispersed in the carrier.

The cleansing gel may additionally contain other, relatively non-thickening but adsorptive powder-form substances distinguished by a large surface, i.e. by a relatively small particle size. Such substances may be inorganic powders such as, for example, talcum, Veegum, zeolites, aluminium oxides or nanoparticulate salts. However, they may also be organic fine-particle adsorbents such as, for example, cellulose, modified starch or polymer powders, such as polyamide powders for example. In a preferred embodiment, the cleansing gel according to the invention contains at least 3% by weight of a particulate inert adsorbent in addition to the compulsory components. A particularly preferred particulate adsorbent is talcum which may be present in the cleansing gel in quantities of 3 to 30% by weight.

In a particularly preferred embodiment, the cleansing gel according to the invention contains

| | |
|---|---|
| 45 to 55% by weight of | a mixture of 1,2-propylene glycol or 1,2-butylene glycol, polyethylene glycol and ethoxydiglycol, |
| 10 to 30% by weight of | dispersed anionic or zwitterionic surfactants, |
| 0.5 to 5% by weight of | dissolved nonionic surfactants, |
| 5 to 20% by weight of | sodium sulfate, magnesium sulfate or aluminium sulfate or a mixture thereof, |
| 0.1 to 0.5% by weight of | dissolved nonionic cellulose ethers, |
| 1 to 5% by weight of | amorphous silica and |
| 3 to 20% by weight of | talcum. |

In addition to the components mentioned, the cleansing gel according to the invention may contain other auxiliaries and additives typical of body cleansing preparations. Additives such as these are intended to improve dermatological compatibility and the general cosmetic sensorial impression. Suitable additives are, for example, moisturizers, such as pyrrolidone carboxylic acid for example, keratolytic and skin-softening components, such as urea and allantoin for example, refatting components, such as emulsified lipid components and silicones for example, dispersed fats and waxes, more particularly those present in microemulsified or nanoparticulate form, vitamins, such as tocopherol, retinol or ascorbic acid, panthenol or biotin, water-soluble protein derivatives, perfumes, dyes and pearlizing pigments.

Other auxiliaries which are mainly intended for stability in storage are, for example, preservatives, complexing agents, pH regulators and buffers.

The cleansing gels according to the invention are produced simply by mixing and heating the components. The liquid carrier components, i.e. the hydroxyl compounds, are introduced first and the thickeners are dissolved or dispersed therein, after which the soluble nonionic surfactants, the powder-form surfactants to be dispersed, the adsorbents and, lastly, the hydrating salts are successively added. It is advisable to carry out production of the gels under a slight reduced pressure in a closed vessel to ensure that no air is trapped in the product and not too much atmospheric moisture is able to enter.

The following Examples are intended to illustrate the invention.

EXAMPLES

The following compositions were prepared (quantities in % by weight):

|  | 1 | 2 | 3 | 4 | 5 |
|---|---|---|---|---|---|
| 1,2-Propylene glycol | — | 25 | 30 | 25 | 25 |
| 1,3-Butylene glycol | 35 | — | — | 5 | — |
| Polyethylene glycol 400 | 10 | 20 | 20 | 15 | 25 |
| Ethoxydiglycol | 8.0 | 10 | 10 | 5.0 | 10 |
| Glycerol | 3.0 | 2.0 | 2.0 | 2.0 | — |
| Dow Corning ® 193 | 1.0 | 1.0 | — | 1.0 | 1.0 |
| Cetiol ® HE | — | 1.0 | 1.5 | — | 2.0 |
| Elfan ® AT 84 | 5.0 | — | 10 | 20 | — |
| Tego Betain ® CKD | — | 15 | 10 | — | 15 |
| Sulfosuccinat 128 P | 15.0 | — | 3.0 | — | 5.0 |
| Perfume oil | 0.3 | 0.3 | 0.3 | 0.3 | 0.3 |
| Klucel ® M | — | 0.2 | 0.2 | 0.3 | 0.3 |
| Steasilk ® 5-GG-HT | 3.7 | 11.3 | — | 16.4 | 4.4 |
| Neosil ® CT 11 | — | 2.5 | — | — | 2.0 |
| Aerosil ® 200 | 4.0 | — | 3.0 | 2.0 | — |
| Na$_2$SO$_4$ | 15 | — | — | — | — |
| MgSO$_4$ | — | 12 | 10.0 | 8.0 | — |
| (Al)$_2$(SO$_4$)$_3$ | — | — | — | — | 10 |
| Viscosity (Pa · s) (Brookfield RTV, spindle D, 20 r.p.m., 20° C.) | 38 | 4 | 11 | 29 | 9 |

The following commercial products were used:
Cetiol® HE (Cognis Deutschland): glycerol+7.3EO cocofatty acid ester
Elfan® AT 84 (Akzo Nobel): cocoacyl isethionate, Na salt (powder, 84% by weight AS)
Tego Betain® CKD (Goldschmidt): cocoacylamidopropyl betaine (powder, 82% by weight AS)
Sulfosuccinat 128 P (Cognis Deutschland): sulfosuccinic acid monofatty alkyl (C$_{12-18}$) ester, disodium salt (powder, 90% AS)
Klucel® M (Hercules): hydroxypropyl cellulose (powder)
Steasilk® 5-GG-HT (Luzenac, Nev.): talcum (powder)
Neosil® CT11 (Crosfield): amorphous silica
Aerosil® 200 (Degussa): pyrogenic amorphous silica

What is claimed is:

1. A cleansing gel composition which releases heat of hydration when mixed with water and which contains a water-free liquid carrier and powder components dispersed therein, comprising
   (A) at least 40% by weight of water-miscible hydroxyl compounds selected from the group consisting of glycols, glycol ethers and polyols containing 2 to 6 carbon atoms and polyalkylene glycols with molecular weights of up to 1,000 D and mixtures thereof,
   (B) at least 5% by weight of surfactants selected from the group consisting of anionic, zwitterionic, and nonionic surfactants,
   (C) at least 5% by weight of dispersed, particulate, water-soluble salts that release heat on mixing with water; and
   (D) at least 0.1% by weight of a water-soluble thickener dissolved in the carrier, or at least 1% by weight of a particulate thickener dispersed in the carrier, or both at least 0.1% by weight of said water-soluble thickener and at least 1% by weight of said particulate thickener.

2. The cleansing gel composition of claim 1, wherein the water-miscible hydroxyl compounds are present in a quantity of 50 to 70%.

3. The cleansing gel composition of claim 1, wherein the composition is comprised of an anionic or zwitterionic surfactant or a mixture of such surfactants in a quantity of 10 to 30% by weight.

4. The cleansing gel composition of claim 1, wherein the water-soluble salts are sodium sulfate, magnesium sulfate, aluminium sulfate or a mixture thereof in a quantity of 5 to 20% by weight.

5. The cleansing gel composition of claim 1, wherein the composition is comprised of a nonionic polysaccharide derivative in a quantity of 0.1 to 1% by weight.

6. The cleansing gel composition of claim 1, wherein the composition is comprised of an amorphous silica in a quantity of 1 to 5% by weight.

7. The cleansing gel composition of claim 1, wherein the composition is additionally comprised of at least 3% by weight of a particulate inert adsorbent.

8. A cleansing gel composition comprising

| | |
|---|---|
| 45 to 55% by weight of | a mixture of (i) propylene glycol or butylene glycol or both propylene glycol and butylene glycol, (ii) polyethylene glycol and (iii) ethoxydiglycol, |
| 10 to 30% by weight of | a dispersed water-free anionic or water-free zwitterionic surfactant or mixture of dispersed water-free anionic and water-free zwitterionic surfactants, |
| 0.5 to 5% by weight of | a dissolved water-free nonionic surfactant, |
| 5 to 20% by weight of | magnesium sulfate, sodium sulfate, or mixture of magnesium sulfate and sodium sulfate |
| 0.1 to 0.5% by weight of | a dissolved nonionic cellulose ether |
| 1 to 5% by weight of | an amorphous silica; and |
| 3 to 20% by weight of | talcum. |

9. The cleansing gel composition of claim 8 comprising an anionic surfactant in the form of a water free fine-particle sodium salt.

10. The cleansing gel composition of claim 8 comprising a zwitterionic surfactant in the form of a water free fine-particle betaine surfactant.

11. The cleansing gel composition of claim 8 wherein the non-ionic surfactant is selected from the group consisting of ethylene oxide addition products of fatty alcohols, ethylene oxide addition products of fatty acids, fatty acid mono- or diglycerides, fatty acid alkanolamides, sorbitan fatty acid esters, methyl glucoside fatty acid esters and alkyl glucosides.

12. The cleansing gel composition of claim 8 wherein no more than 15% by weight of magnesium sulfate is present.

13. The cleansing gel composition of claim 8 wherein amorphous silica is present as a pyrogenic silica or a fine-particle silica gel.

\* \* \* \* \*

UNITED STATES PATENT AND TRADEMARK OFFICE
CERTIFICATE OF CORRECTION

PATENT NO.     : 6,641,825 B2
DATED          : November 4, 2003
INVENTOR(S)    : Scholz et al.

It is certified that error appears in the above-identified patent and that said Letters Patent is hereby corrected as shown below:

Column 5,
Line 48, after "of", insert -- water-free --.

Signed and Sealed this

Twenty-third Day of November, 2004

JON W. DUDAS
*Director of the United States Patent and Trademark Office*